(12) United States Patent
Choi et al.

(10) Patent No.: US 10,010,290 B2
(45) Date of Patent: Jul. 3, 2018

(54) SIGNAL PROCESSING APPARATUS, SIGNAL RECOVERY APPARATUS, SIGNAL PROCESSING METHOD, AND SIGNAL RECOVERY METHOD

(71) Applicant: Samsung Electronics Co., Ltd., Suwon-si, Gyeonggi-do (KR)

(72) Inventors: Byung-Kwon Choi, Suwon-si (KR); Keehong Seo, Seoul (KR); Youngbo Shim, Seoul (KR); Taesin Ha, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 47 days.

(21) Appl. No.: 14/696,723

(22) Filed: Apr. 27, 2015

(65) Prior Publication Data

US 2016/0149694 A1 May 26, 2016

(30) Foreign Application Priority Data

Nov. 24, 2014 (KR) .................. 10-2014-0164694

(51) Int. Cl.
| | |
|---|---|
| H04L 7/00 | (2006.01) |
| A61B 5/00 | (2006.01) |
| G01R 25/00 | (2006.01) |
| H04Q 9/00 | (2006.01) |
| A61B 5/11 | (2006.01) |

(52) U.S. Cl.
CPC ............ *A61B 5/6801* (2013.01); *A61B 5/112* (2013.01); *A61B 5/7235* (2013.01); *G01R 25/00* (2013.01); *H04Q 9/00* (2013.01); *A61B 5/1122* (2013.01); *A61B 5/6828* (2013.01)

(58) Field of Classification Search
CPC .... H04L 7/0087; H04L 7/0054; H04L 7/0029
See application file for complete search history.

(56) References Cited

U.S. PATENT DOCUMENTS

| | | | |
|---|---|---|---|
| 4,975,915 A | 12/1990 | Sako et al. | |
| 5,239,470 A | 8/1993 | Komatsu | |
| 5,298,899 A * | 3/1994 | Oh ..................... | H03M 7/3002 341/132 |
| 5,479,168 A | 12/1995 | Johnson et al. | |
| 6,009,549 A | 12/1999 | Bliss et al. | |
| 7,698,249 B2 | 4/2010 | Buyuktosunoglu et al. | |
| 8,156,403 B2 | 4/2012 | Shalvi et al. | |
| 8,579,827 B1 | 11/2013 | Rulkov et al. | |

(Continued)

FOREIGN PATENT DOCUMENTS

| | | | |
|---|---|---|---|
| JP | 5183534 B2 | 4/2013 | |
| JP | 5350393 B2 | 11/2013 | |

(Continued)

*Primary Examiner* — Jaison Joseph
(74) *Attorney, Agent, or Firm* — Harness, Dickey & Pierce, P.L.C.

(57) ABSTRACT

A method and apparatus for processing a signal, wherein the apparatus identifies a sample interval satisfying a predetermined reference using a change in a plurality of samples based on a downsampling, acquires, based a result of the identifying, a feature point of a signal before the downsampling is applied to the signal, and acquires time information corresponding to a position of the feature point in a feature sample interval including the feature point is provided.

15 Claims, 9 Drawing Sheets

(56) References Cited

U.S. PATENT DOCUMENTS

| | | | |
|---|---|---|---|
| 2009/0281462 A1* | 11/2009 | Heliot .................. | A61B 5/1038 600/595 |
| 2010/0010650 A1* | 1/2010 | Ooue ............... | G11B 20/10009 700/94 |
| 2010/0125229 A1* | 5/2010 | Rudolph .............. | A61B 5/1038 602/16 |
| 2012/0089390 A1* | 4/2012 | Yang ...................... | G10H 1/366 704/207 |
| 2012/0209149 A1* | 8/2012 | Yoneyama ............. | A61B 5/112 600/595 |

FOREIGN PATENT DOCUMENTS

| | | |
|---|---|---|
| JP | 5388542 B2 | 1/2014 |
| KR | 100536672 B1 | 12/2005 |
| KR | 100982282 B1 | 9/2010 |

\* cited by examiner

SIGNAL PROCESSING APPARATUS, SIGNAL RECOVERY APPARATUS, SIGNAL PROCESSING METHOD, AND SIGNAL RECOVERY METHOD

CROSS-REFERENCE TO RELATED APPLICATION

This application claims the priority benefit of Korean Patent Application No. 10-2014-0164694, filed on Nov. 24, 2014, in the Korean Intellectual Property Office, the entire contents of which are incorporated herein by reference in its entirety.

BACKGROUND

1. Field

Example embodiments relate to walking assist device.

2. Description of the Related Art

When analyzing a signal, it may be desirable to know signal features such as a maximum value and/or a minimum value of the signal. For example, the maximum value or the minimum value of a signal sensed by a walking assistance device may indicate gait characteristics of a user wearing the walking assistance device. However, when a signal is sampled, the maximum value and/or the minimum value may be lost in the sampled signal. Accordingly, there is a desire for a method of preventing a loss of a signal feature.

SUMMARY

Some example embodiments relate to a signal processing apparatus.

In some example embodiments, the apparatus may include an identifier configured to identify a sample interval satisfying a predetermined reference using a change in a plurality of samples based on a downsampling, an acquirer configured to acquire, based a result of the identifying, a feature point of a signal before the downsampling is applied to the signal, and acquire time information corresponding to a position of the feature point in a feature sample interval including the feature point, and a generator configured to generate a data stream including the feature point and the time information.

The acquirer may be configured to acquire a time difference between the feature point and an interval reference sample of the feature sample interval.

The generator may be configured to generate the data stream by applying the feature point and the time information as an interval reference sample of the feature sample interval.

The signal processing apparatus may further include an amplifier configured to amplify the time information based on a predetermined scheme.

The signal processing apparatus may be configured to transmit the data stream to a remote apparatus through a communication interface.

The signal may include a signal sensed based on a motion of a user wearing a device including the signal processing apparatus.

The signal processing apparatus may be embedded in a walking assistance device.

The feature point may include an inflection point of the signal.

Other example embodiments relate to a signal recovery apparatus.

In some example embodiments, the apparatus may include a receiver configured to receive a data stream from an external apparatus, a detector configured to detect a feature point of a signal sensed by the external apparatus based on data acquired from the data stream, and time information on the feature point, and an interpolator configured to determine an index of the feature point based on the time information, and perform interpolation on the data based on a result of the determining.

The signal recovery apparatus may further include an upsampler configured to apply an upsampling to the acquired data.

The external apparatus may include a walking assistance device.

The signal recovery apparatus may further include an output unit configured to output data restored through the interpolation.

The signal recovery apparatus may further include an analyzer configured to analyze walking features of a user wearing the external apparatus based on data restored through the interpolation.

Other example embodiments relate to a signal processing method.

In some example embodiments, the method may include identifying a sample interval satisfying a predetermined reference using a change in a plurality of samples based on a downsampling, acquiring, based a result of the identifying, a feature point of a signal before the downsampling is applied to the signal, and acquire time information corresponding to a position of the feature point in a feature sample interval including the feature point, and generating a data stream including the feature point and the time information.

Other example embodiments relate to a signal recovery method.

In some example embodiments, the method may include receiving a data stream from an external apparatus, acquiring a feature point of a signal sensed by the external apparatus based on data acquired from the data stream, and time information on the feature point, and determining an index of the feature point based on the time information and performing interpolation on the data based on a result of the determining.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Hereinafter, some example embodiments will be described in detail with reference to the accompanying drawings, in which some example embodiments are shown. In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

Unless otherwise defined, all terms including technical and scientific terms used herein have the same meaning as commonly understood by one of ordinary skill in the art to which the exemplary embodiments belong. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Various example embodiments will now be described more fully with reference to the accompanying drawings in which some example embodiments are shown. In the drawings, the thicknesses of layers and regions are exaggerated for clarity.

Figure 1:
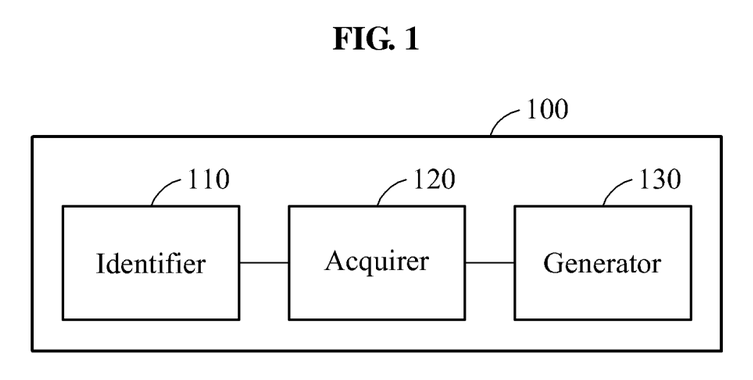
FIG. 1 illustrates a signal processing apparatus according to example embodiments.

FIG. 1 illustrates a signal processing apparatus 100 according to example embodiments.

The signal processing apparatus 100 may be provided in the form of an independent device, for example, a stand-alone device. Also, the signal processing apparatus 100 may be embedded in an electronic device, for example, a walking assistance device, a mobile terminal, and/or a wearable device, or connected thereto using a communication interface.

Referring to FIG. 1, the signal processing apparatus 100 may include an identifier 110, an acquirer 120, and a generator 130.

The signal processing apparatus 100 may include a processor and a memory (not shown).

The memory may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM).

The processor may be, a central processing unit (CPU), a controller, or an application-specific integrated circuit (ASIC), that when, executing instructions stored in the memory, configures the processor as a special purpose computer to perform the operations of one or more of the identifier 110, acquirer 120, and generator 130. For example, the signal processing apparatus 100 may perform the operations illustrated in FIG. 7 such that the signal processing apparatus 100 generates a data stream by incorporating, into a sampled signal, information on a time difference between each of a minimum and maximum values of the sampled signal and respective reference samples preceding the minimum and maximum values. The signal processing apparatus 100 may improve the functioning of the computer itself by reducing the quantity information transmitted in the data stream through downsampling, thereby reducing the probability of an error in transmission of the data stream while still allowing the data stream to be correctly recovered.

The signal processing apparatus 100 may sense user motion information using a sensor (not shown). The sensor may sense, for example, a walking speed, a number of steps, and/or a joint angle, for example, a joint degree of a hip joint, which changes based on a gait of a user. Also, the signal processing apparatus 100 may receive an output value of the sensing from the sensor through a communication interface (not shown). The communication interface may include, for example, a wireless Internet interface such as a wireless local area network (WLAN), a wireless fidelity (WiFi) Direct, a digital living network alliance (DLNA), a wireless broadband (WiBro), a world interoperability for microwave access (WiMAX), a high speed downlink packet access (HSDPA), and the like, and a local area communication interface such as a Bluetooth, a radio frequency identification (RFID), an infrared data association (IrDA), an ultra wideband (UWB), ZigBee, a near field communication (NFC), and the like. Also, the communication interface may indicate any interface, for example, a wired interface, to communicate with an external apparatus.

The sensor may output a sampled signal. For example, the sensor may output a signal sampled at a rate of 100 hertz (Hz).

The signal processing apparatus 100 may further include a downsampler (not shown) configured to downsample the sampled signal at a sample interval. As an example, the downsampler may downsample the 100 Hz input signal based on a downsampling rate, for example, 50 Hz or 25 Hz. When an input signal is downsized, a number of samples in the signal may change. For example, when the 100 Hz input signal is downsampled at 50 Hz, 50 samples may be extracted from the 100 samples per second input signal.

The identifier 110 may determine the sample interval satisfying a desired (or, alternatively, a predetermined) reference based on a change in a plurality of samples due to the downsampling. The reference may include, for example, at least one of a reference of the plurality of samples changing from a positive value to a negative value and a reference of the plurality of samples changing from the negative value to the positive value.

For example, six samples A, B, C, D, E, and F may be extracted from 12 samples A, a, B, b, C, c, D, d, E, e, F, and f through the downsampling. When a change between the sample A and the sample B is a positive value, and when a change between the sample B and the sample C is a negative value, the sample B may be a point at which the samples change from the positive value to the negative value. The identifier 110 may identify a sample interval between the sample A and the sample C satisfying the reference.

In the above example, when a change between the sample D and the sample E is a negative value, and when a change between the sample E and the sample F is a positive value, the sample E may be a point at which the samples are changed from the negative value to a positive value. The identifier 110 may identify a sample interval between the sample D and the sample F satisfying the reference.

The acquirer 120 may acquire a feature point of a signal sampled in the identified sample interval.

The acquirer 120 may verify sample values of samples included in the identified sample intervals. For example, as discussed above, a value of the sampled signal may increase between the intervals from A to B and decrease between B to C. The acquirer 120 may verify sample values of samples between A to B and between B to C.

For example, the sample "a" may be included in a sample interval between the sample A and the sample B, and the sample "b" may be included in a sample interval between the sample B and the sample C. Therefore, to acquire a maximum value, the acquirer 120 may verify a sample value of the sample "a" included in the sample interval between the sample A and the sample B. Also, to acquire the maximum value, the acquirer 120 may verify a sample value of the sample "b" included in the sample interval between the sample B and the sample C. The acquirer 120 may determine that the sampled signal has a maximum value in the sample "a".

Likewise, as discussed above, the value of the sampled signal may decrease between the intervals from D to E and increase from E to F.

To acquire a minimum value, the acquirer 120 may verify a sample value of the sample "d" included in the sample interval between the sample D and the sample E. Also, to acquire the minimum value, the acquirer 120 may verify a sample value of the sample "e" included in the sample interval between the sample E and the sample F. The acquirer 120 may determine that the sampled signal has the minimum value in the sample "e".

The acquirer 120 may acquirer time information corresponding to the feature point in a feature sample interval including the feature point.

The acquirer 120 may acquire a time difference between the feature point and an interval reference sample of the feature sample interval. The interval reference sample may include a start sample indicating a start of the feature sample interval and an end sample indicating an end of the feature sample interval. The acquirer 120 may acquire a time difference between the feature point and the start sample of the interval reference sample. Also, the acquirer 120 may acquire a time difference between the feature point and the end sample of the interval reference sample. The acquirer 120 may acquire a degree of the feature point shifted from the interval reference sample.

For example, the acquirer 120 may acquire a time difference between the sample A and the sample "a". Since a sample interval between the sample A and the sample "a" is "1", the acquirer 120 may determine the time difference as "1". Also, the acquirer 120 may acquire a time difference between the sample B and the sample b. Since a sample interval between the sample B and the sample "b" is "1", the acquirer 120 may determine the time difference as "1". Based on the time difference, the acquirer 120 may acquire positional information on the feature point in the feature sample interval.

The generator 130 may generate a data stream including the feature point and the time information.

In the above example, the six samples A, B, C, D, E, and F may be extracted through the downsampling. The six sampled A, B, C, D E, and F extracted from the input signal through downsampling may not include one or more of the maximum value and the minimum value of the sampled signal. For example, the sample "a" and the sample "e" may not be included in the samples based on the downsampling. Therefore, conventionally, when the sample values of the samples A, B, C, D, E, and F are transmitted to a corresponding apparatus, and when the samples A, B, C, D, E, and F are restored in the corresponding apparatus, the feature point may not be restored.

In contrast, in one or more example embodiments, the generator 130 may generate the data stream by incorporating the time information and the sample value of the sample "a" in the data stream in lieu of the sample values of the sample A and the sample B of the feature sample interval including the sample "a". Also, the generator 130 may generate the data stream by incorporating the time information and the sample value of the sample "e" in the data stream in lieu of the sample values of the sample E and the sample F of the feature sample interval including the sample "e". For example, the generator 130 may generate the data stream including the sample value of the sample "a", the time information on the sample "a", the sample values of the sample B through the sample D, the sample value of the sample "e", and the time information on the sample e". The generator 130 may generate the data stream based on the time information and the sample value of the feature point in lieu of the sample values of the start sample and the end sample.

In an example, the generator 130 may amplify the time information based on a desired (or, alternatively, a predetermined) scheme, and incorporate the amplified time information in the data stream. In response to the amplifying, an apparatus receiving the data stream may more easily detect the time information. In the above example, time information corresponding to "1" may be included in the generated data stream. The generator 140 may amplify the time information by a factor of two times the maximum value. For example, replace the time information of "1" with "(maximum value×2)+1" in the data stream by adding "maximum value×2" to the time information. Among data included in the data stream, data including the time information may have the maximum value.

The signal processing apparatus 100 may transmit the generated data stream to the corresponding apparatus through the communication interface. The communication interface may include the wireless interface, for example, a Bluetooth module, as described above. The corresponding apparatus may be, for example, a stationary terminal such as a personal computer (PC) and the like. The stationary terminal may include a display to display data obtained by restoring the data stream.

Figure 2:
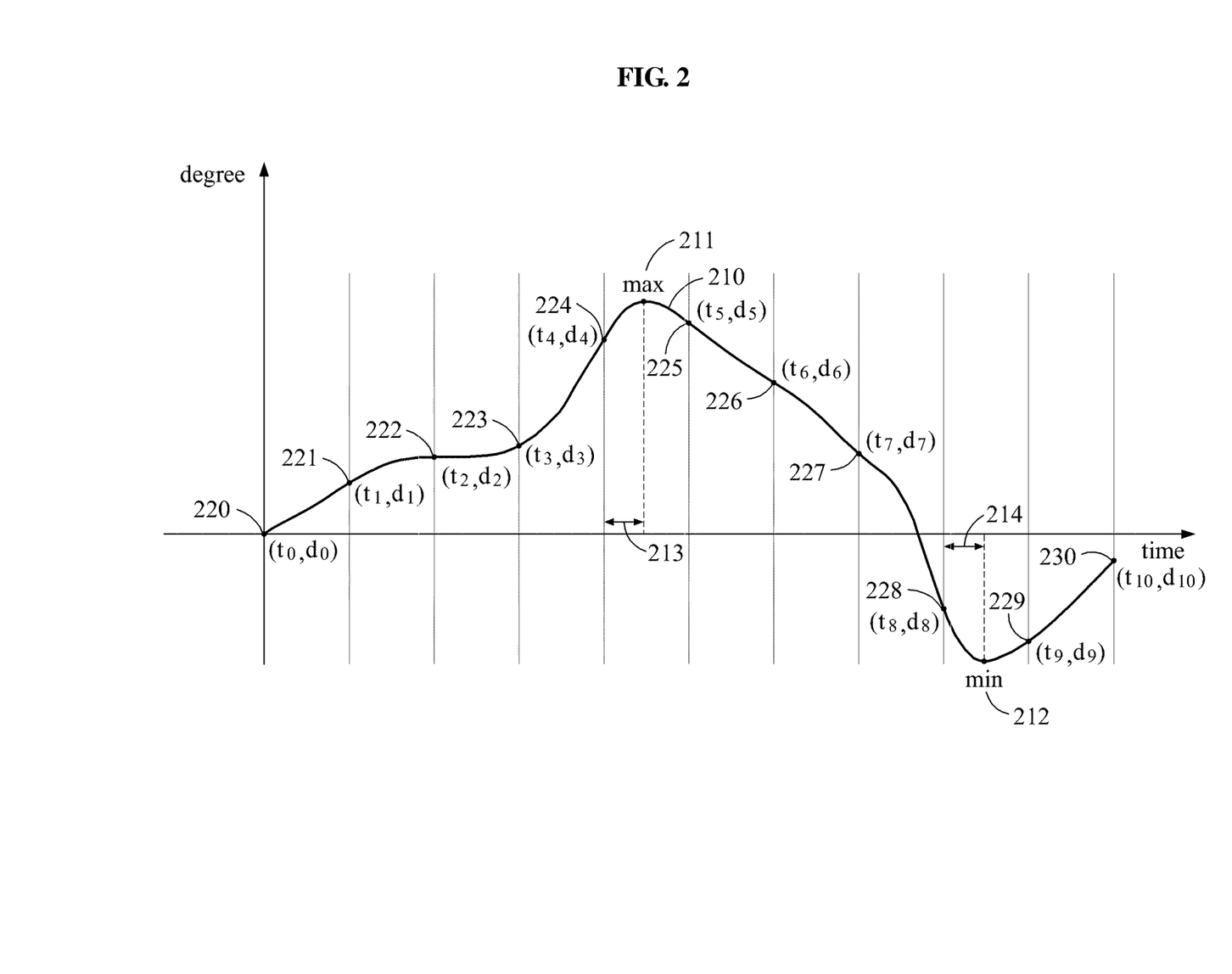
FIG. 2 illustrates a signal processed by a signal processing apparatus according to example embodiments.

FIG. 2 illustrates a signal processed by a signal processing apparatus according to example embodiments.

Referring to FIG. 2, the signal processing apparatus may process a joint angle signal of a hip joint sensed based on a gait of a user wearing a walking assistance device such that in the graph of FIG. 2, an x axis represents a time, and a y axis represents a joint degree of the hip joint.

FIG. 2 illustrates a sampled signal 210 and samples 220 through 230 based on a downsampling. Although FIG. 2 illustrates the sampled signal 210 as a consecutive signal, the sampled signal 210 may be a discrete signal including a plurality of samples in practice.

The signal processing apparatus may identify a sample interval satisfying a desired (or, alternatively, a predetermined) reference using a change in a plurality of samples based on the downsampling. The signal processing apparatus may verify a gradient between the sample 224 and the sample 225, and a gradient between the sample 225 and the sample 226. Based on a result of the verifying, the signal processing apparatus may verify a sample value for each of a plurality of samples included between the sample 224 and the sample 226, and detect a maximum value 211 based on a result of the verifying. Also, a feature sample interval including the maximum value 211 may be identified in response to the verifying of the maximum value 211. In this example, the feature sample interval may be a sample interval between the sample 224 and the sample 225, and each of the sample 224 and the sample 225 may be used as an interval reference sample.

The signal processing apparatus may acquire information on a distance between the maximum value 211 and the sample 224. For example, the signal processing apparatus may acquire the information 213 on a time difference 213 between the maximum value 211 and the sample 224. Also, the signal processing apparatus may acquire information on a distance between the maximum value 211 and the sample 225.

The signal processing apparatus may verify a gradient between the sample 227 and the sample 228, and a gradient between the sample 228 and the sample 229. Based on a result of the verifying, the signal processing apparatus may verify a sample value for each of a plurality of samples included between the sample 227 and the sample 229, and detect a minimum value 212 based on the verified sample value. Also, a feature sample interval including the minimum value 212 may be identified based on a result of the verifying of the minimum value 212. In this example, the feature sample interval may be a sample interval between the sample 228 and the sample 229, and each of the sample 228 and the sample 229 may be used as an interval reference sample of the feature sample interval.

The signal processing apparatus may acquire information on a distance between the minimum value 212 and the sample 228. For example, the signal processing apparatus may acquire the information on a time difference 214 between the minimum value 212 and the sample 228. Also, the signal processing apparatus may acquire information on a distance between the minimum value 212 and the sample 229.

The signal processing apparatus may generate a data stream by incorporating into the sampled signal information on the time difference between each of the minimum and maximum values and their respective interval reference samples. In an example of FIG. 2, the signal processing apparatus may incorporate the information on the time difference 213 and the maximum value 211 in the data stream in lieu of the sample values of the sample 224 and the sample 225. Also, the signal processing apparatus may incorporate the information on the time difference 214 and the minimum value 212 in the data stream in lieu of the sample values of the sample 228 and the sample 229.

The generated data stream may be transmitted to a signal recovery apparatus through a wired network or a wireless network. The signal recovery apparatus may decode the data stream and perform a recovery procedure.

Figure 3:
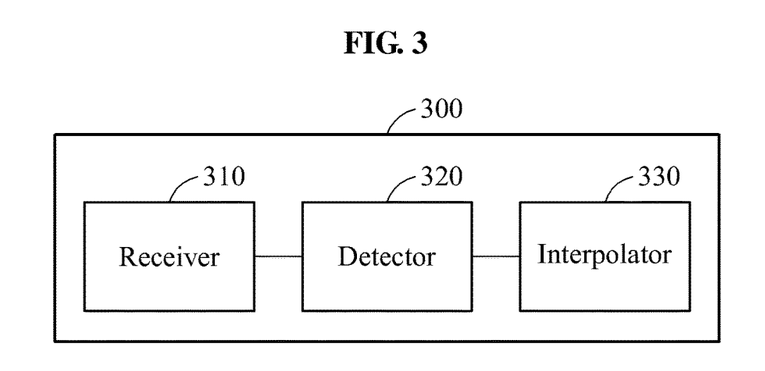
FIG. 3 illustrates a signal recovery apparatus according to example embodiments.

FIG. 3 illustrates a signal recovery apparatus 300 according to example embodiments.

The signal recovery apparatus 300 may be implemented as an independent device, for example, a standalone device. Also, the signal recovery apparatus 300 may be embedded in a stationary terminal such as a PC or in a mobile terminal such as a laptop computer, and may be connected through a communication interface.

The signal recovery apparatus 300 may include a receiver 310, a detector 320, and an interpolator 330.

The signal recovery apparatus 300 may include a processor and a memory (not shown).

The memory may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM).

The processor may be, a central processing unit (CPU), a controller, or an application-specific integrated circuit (ASIC), that when, executing instructions stored in the memory, configures the processor as a special purpose computer to perform as one or more of the receiver 310, detector 320, interpolator 330. For example, the instructions may configure the processor to perform the operations illustrated in FIG. 8 such that the signal recovery apparatus 300 interpolates data in a data stream to recover a signal that correctly represents the minimum and maximum thereof.

The receiver 310 may receive a data stream from an external apparatus. The external apparatus may include, for example, a walking assistance device. The walking assistance device may sense a motion, for example, a moving speed and/or a joint degree of a hip joint, from a user. Subsequently, the walking assistance device may process sensed information, and transmit the processed information to the signal recovery apparatus 300 as a data stream.

The receiver 310 may include a communication interface to communicate with the external device. The communication interface may include, for example, a wireless Internet interface such as a WLAN, a WiFi Direct, a DLNA, a WiBro, a WiMAX, a HSDPA, and the like, and a local area communication interface such as a Bluetooth, an RFID, an IrDA, a UWB, ZigBee, an NFC, and the like. Also, the communication interface may indicate any interface, for example, a wired interface, to communicate with the external apparatus. From the received data stream, the signal recovery apparatus 300 may acquire data including, for example, a sample value of a signal, a feature point of the signal, and time information on the feature point.

The signal recovery apparatus 300 may include an upsampler. The upsampler may apply an upsampling to the acquired data.

As an example, the signal recovery apparatus 300 may acquire "0, 2, 4, 6, 9, 19, 6, 4, 2, and 0" from the data stream. When a raw signal includes 20 samples, the upsampler may add samples among the acquired data through the upsampling. The sample may be added between "0" and "2", and between "2" and "4". The values of the added samples may be determined by the interpolator 330 described below.

The detector 320 may detect the feature point of the signal and the time information on the feature point based on the data acquired from the data stream. As an example, the detector 320 may detect the feature point and the time information on the feature point based on a change in the acquired data. The detector 320 may verify the change in the data, and identify an interval satisfying a desired (or, alternatively, a predetermined) reference. In the above example, a gradient may be changed from a positive value to a negative value in intervals of "9", "19", and "6". "19" may be a point at which the gradient changes from the positive value to the negative value, and may be a value obtained by processing the time information on the feature point using the external apparatus based on a desired (or, alternatively, predetermined) scheme such that the signal recovery apparatus 300 more easily detects the time information on the feature point.

The detector 320 may determine data having a greatest value among the acquired data as the time information. The signal recovery apparatus 300 and the external apparatus may share information about generating of "19". Also, the detector 320 may determine a greatest value of remaining data obtained by excluding the point at which the gradient is changed, as a maximum value. In the above example, the detector 320 may acknowledge that "19" is generated based on "2*maximum value+time information". Therefore, the time information may be determined to be "9".

The interpolator 330 may determine an index of the feature point based on the time information on the feature point. In the above example, an index of "9" corresponding to the feature point may be index "5" among 10 items of the acquired data, "0, 2, 4, 6, 9, 19, 6, 4, 2, and 0". When the upsampling is applied based on a desired (or, alternatively, a predetermined) upsampling rate, one sample may be added between each of the samples. In a case of adding the one sample, the index of "9" corresponding to the feature point may be "9". The interpolator 330 may shift the index of the feature point to which the upsampling is applied, based on the time information. In the above example, since the time information on the feature point is "1", the interpolator 330 may determine the index of the feature point as "10". In response to the determining, the interpolator 330 may perform an interpolation on the acquired data. Through the interpolation, the interpolator 330 may restore values "1, 3, 5, 7, 8, 8, 7, 5, 3, and 1" between each of the acquired pieces of data acquired data, "0, 2, 4, 6, 9, 19, 6, 4, 2, and 0" through linear interpolation. Therefore, the interpolator 330 may determine sample values for samples of which sample values are not determined. In the above example, a raw signal of "0, 1, 2, 3, 4, 5, 6, 7, 8, 9, 8, 7, 6, 5, 4, 3, 2, 1, and 0" may be recovered through the interpolation.

In an example, the signal recovery apparatus 300 may include an output unit to output the data restored through the interpolation. The output unit may visually indicate the restored data. For example, a display may display the restored data using a graph.

In an example, the signal recovery apparatus 300 may further include an analyzer (not shown) to analyze gait characteristics of a user wearing the external apparatus, based on the data restored through the interpolation. The analyzer may analyze, for example, a gait pattern, a gait speed, an extension degree of a hip joint, and a flexion degree of the hip joint of the user based on the restored data.

Figure 4:
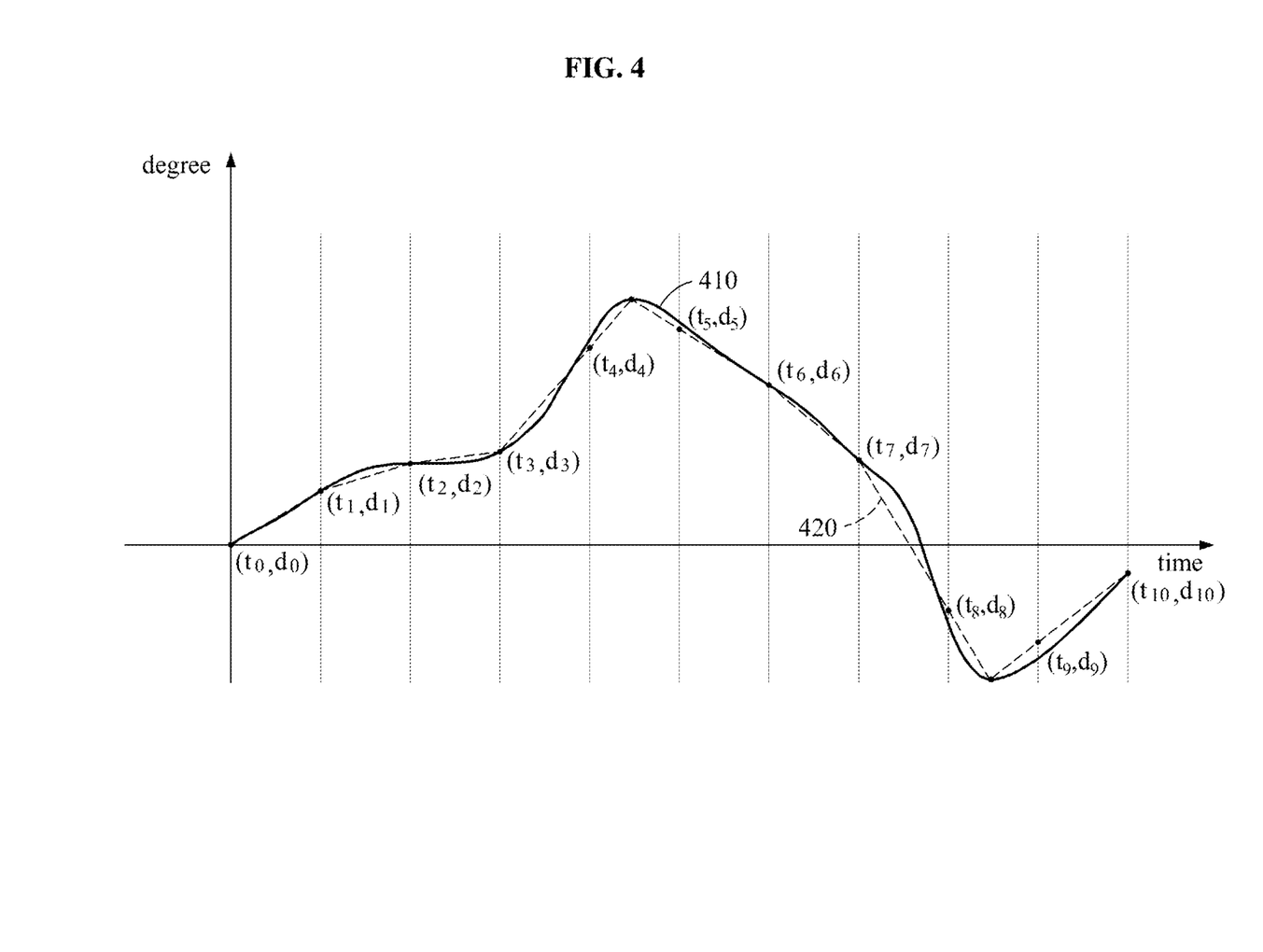
FIG. 4 illustrates an example of recovering a signal using a signal recovery apparatus according to example embodiments.

FIG. 4 illustrates an example of recovering a signal using a signal recovery apparatus according to example embodiments.

FIG. 4 illustrates a raw signal 410 and a recovered signal 420. The raw signal 410 may be a signal sensed based on a gait of a user wearing a walking assistance device. Although FIG. 4 illustrates the raw signal 410 as a consecutive signal, the raw signal 410 may be, for example, a discrete signal including a plurality of samples.

The walking assistance device may perform a downsampling to reduce a quantity of data in the raw signal 410. When the downsampling is performed, a maximum value and/or a minimum value of the raw signal 410 may be lost. To prevent a loss of the maximum value and the minimum value, the walking assistance device may transmit, to a signal recovery apparatus, information indicating the maximum value and a distance between the maximum value and t4. Also, the walking assistance device may transmit, to the signal recovery apparatus, information indicating the minimum value and a distance between the minimum value and t8. The signal recovery apparatus may restore the maximum value and the minimum value of the raw signal 410 based on the information received from the walking assistance device.

As shown in an interval (t4, t5), the recovered signal 420 may include the maximum value of the raw signal 410. Also, as shown in an interval (t8, t9), the recovered signal 420 may include the minimum value of the raw signal 410.

FIGS. 5A through 5D illustrate examples of a raw signal 510, a signal 520 recovered through a linear interpolation, and a signal 530 recovered according to example embodiments.

Referring to FIGS. FIGS. 5A through 5D, an x axis represents time, and a y axis represents a joint degree of a hip joint changing based on a gait of a user. Hereinafter, the signal 520 recovered through a linear interpolation may be referred to as a first recovered signal 520, and the signal 530 recovered according to example embodiments may be referred to as the recovered signal 530, respectively.

Differing downsampling rates may be applied to the raw signal 510. For example, a downsampling rate may increase from FIG. 5A to FIG. 5D. As discussed in more detail below, as the downsampling rate increases, the second recovered signal 530 may more accurately reproduce the raw signal 510 than the first recovered signal 520.

Figure 5A:
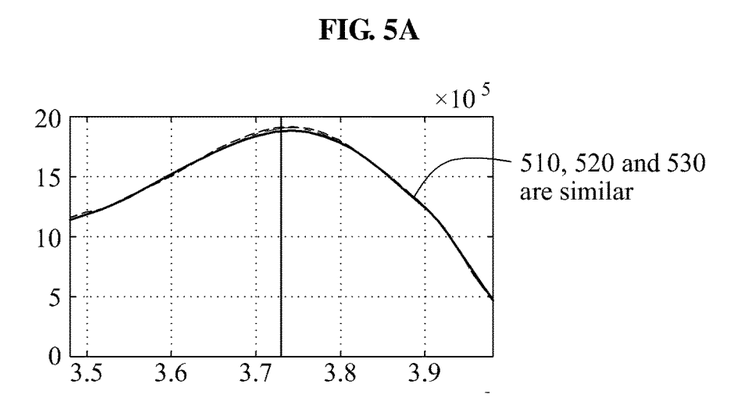
FIGS. 5A through 5D illustrate examples of a raw signal, a signal recovered through a linear interpolation, and a signal recovered according to example embodiments.

Referring to FIG. 5A, the raw signal 510, the first recovered signal 520 and the second recovered signal 530 may be similar to one another.

Figure 5B:
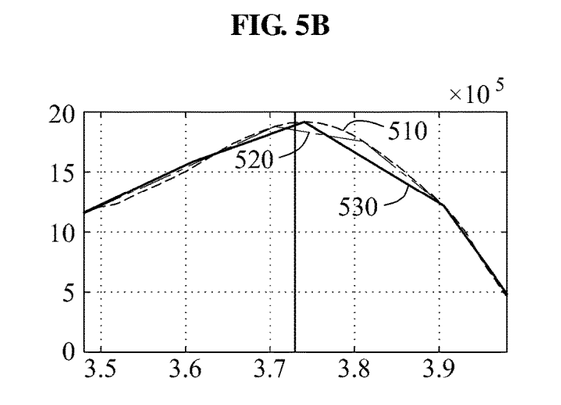

Referring to FIG. 5B, the raw signal 510 and the first recovered signal 520 may be similar to one another while a maximum value of the raw signal 510 is inaccurately restored.

Figure 5C:
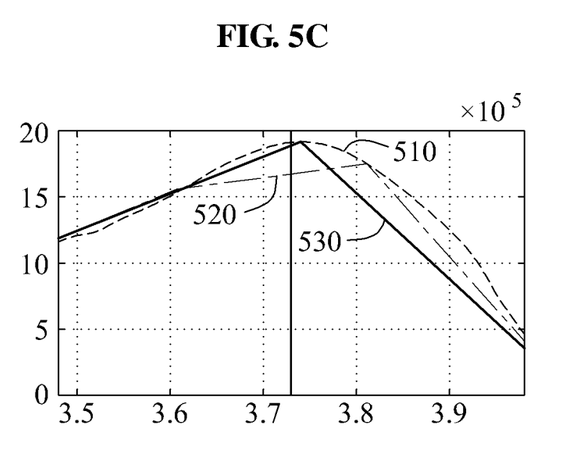

Referring to FIG. 5C, the raw signal 510, the first recovered signal 520, and the second recovered signal 530 are similar to one another in a time interval before the maximum value occurs. However, the first recovered signal 520 may inaccurately express the maximum value of the raw signal 510, while the second recovered signal 530 may accurately express the maximum value of the raw signal 510.

Figure 5D:
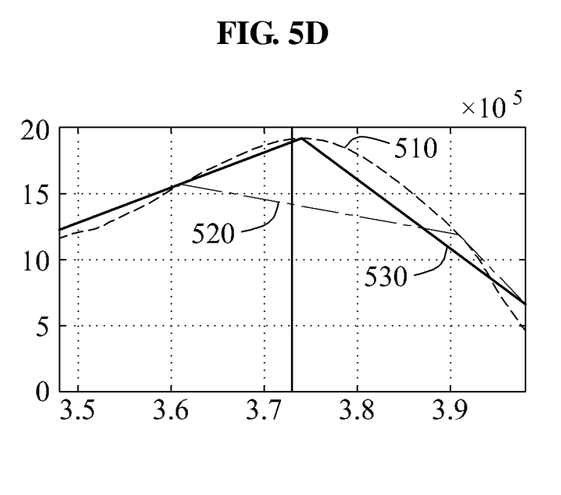

Referring to FIG. 5D, a greatest downsampling rate may be applied to the raw signal 510. A degree of losing the maximum value of the raw signal 510 in the recovered signal 520 may increase according to an increase in the downsampling rate. However, the recovered signal 530 may accurately express the maximum value of the raw signal 510 despite the increase in the downsampling rate.

Figure 6:
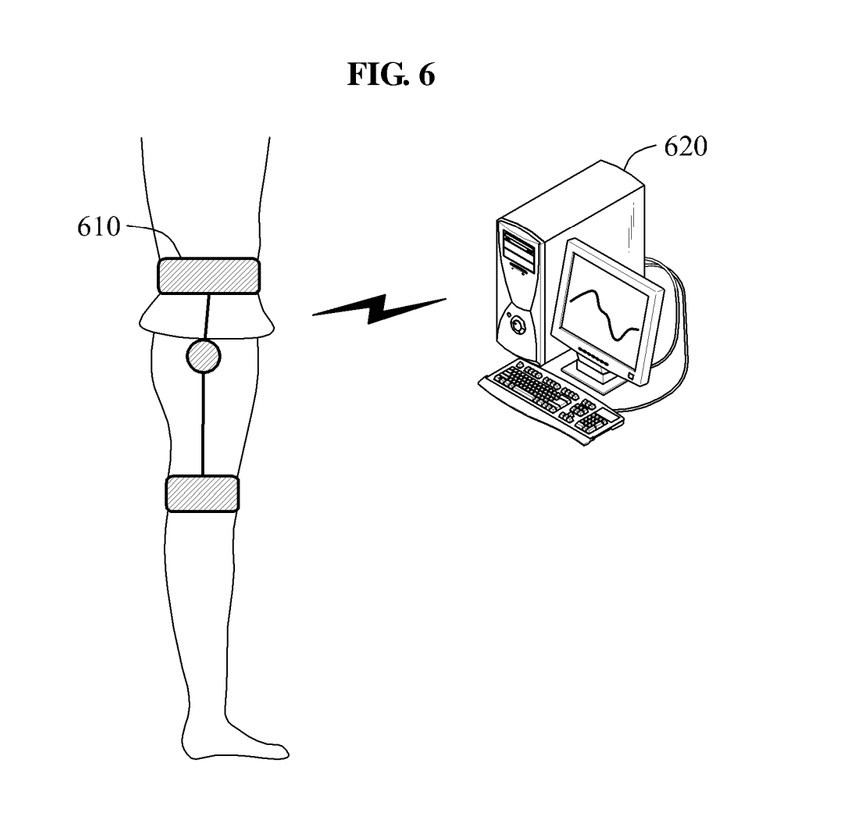
FIG. 6 illustrates a system including a signal recovery apparatus and a signal processing apparatus according to example embodiments.

FIG. 6 illustrates a system including a signal recovery apparatus and a signal processing apparatus according to example embodiments.

Referring to FIG. 6, the signal processing apparatus may be embedded in a walking assistance device 610. FIG. 6 illustrates the walking assistance device 610 as a hip-type walking assistance device. However, a type of the walking assistance device 610 is not limited thereto. For example, the walking assistance device 610 may include, for example, a walking assistance device that supports an entire lower limb, and a walking assistance device that supports a portion of a lower limb. Also, the walking assistance device 610 may include, for example, a walking assistance device that supports a portion of a lower limb down to a knee, and a walking assistance device that supports a portion of a lower limb down to an ankle.

The walking assistance device 610 may include a driving motor to drive joint portions of the walking assistance device 610 so as to support a muscular strength of a lower limb for a user. For example, the walking assistance device 610 may include two motors to deliver driving force to both hip-joint portions.

The walking assistance device 610 may use a sensor (not shown) to acquire a joint degree of a hip joint changing based on a gait of a user. The walking assistance device 610 may transmit, to a signal recovery apparatus 620, information, for example, motor information and torque information, as well as the acquired joint degree.

When various items of information are simultaneously transmitted to the signal recovery apparatus 620, an error may occur due to communication interference. The walking assistance device 610 may reduce a quantity of the information through a downsampling, thereby reducing the probability of an error in transmission. When the walking assistance device 610 performs the downsampling, a feature point of a sensed signal may be lost and thus, the walking assistance device 610 and/or the signal recovery apparatus 620 may perform a signal processing to prevent a loss of the feature point.

The signal recovery apparatus 620 may restore data transmitted from the walking assistance device 610. The restored data may include the feature point of the signal sensed by the walking assistance device 610. Based on the feature point, gait characteristics such as a flexion degree of a hip joint of a user may be analyzed accurately.

Figure 7:
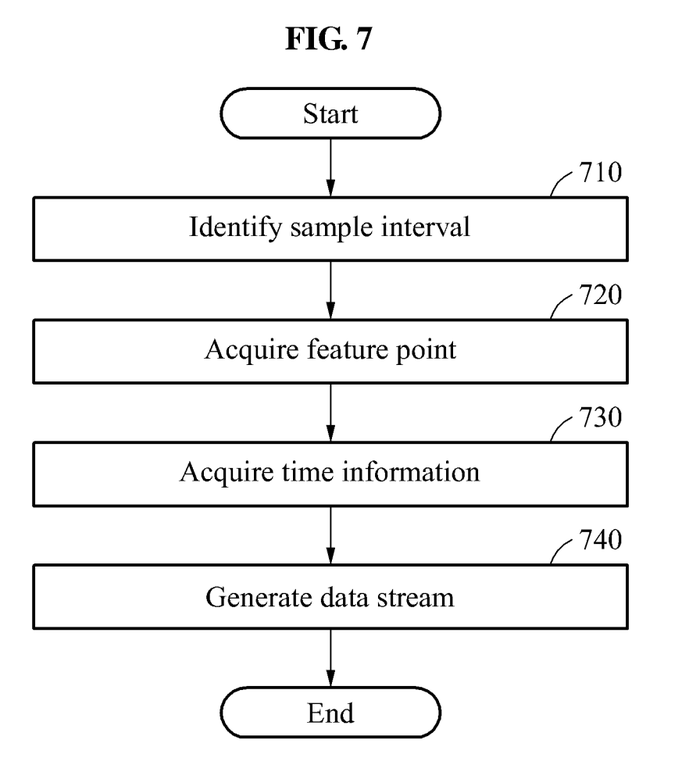
FIG. 7 illustrates a signal processing method according to example embodiments.

FIG. 7 illustrates a signal processing method according to example embodiments.

The signal processing method may be performed by a signal processing apparatus.

In operation 710, the signal processing apparatus identifies a sample interval satisfying a desired (or, alternatively, a predetermined) reference using a change in a plurality of samples based on a downsampled signal.

In operation 720, based on a result of the identifying, the signal processing apparatus acquires a feature point of the signal before the downsampling is applied.

In operation 730, the signal processing apparatus acquires time information corresponding to a position of the feature point in a feature sample interval including the feature point. For example, the signal processing apparatus may acquire a time difference between the feature point and an interval reference sample of the feature sample interval. In this example, the interval reference sample may include a start sample and an end sample of the feature sample interval.

In operation 740, the signal processing apparatus generates a data stream including the feature point and the time information. The signal processing apparatus may generate the data stream using the feature point and the time information in lieu of the interval reference sample of the feature sample interval.

In an example, the signal processing apparatus may amplify the time information based on a desired (or, alternatively, a predetermined) scheme. Also, the signal processing apparatus may transmit the data stream to a remote apparatus through a communication interface.

Since the descriptions provided with reference to FIGS. 1 through 6 are also applicable here, repeated descriptions with respect to FIG. 7 will be omitted for increased clarity and conciseness.

Figure 8:
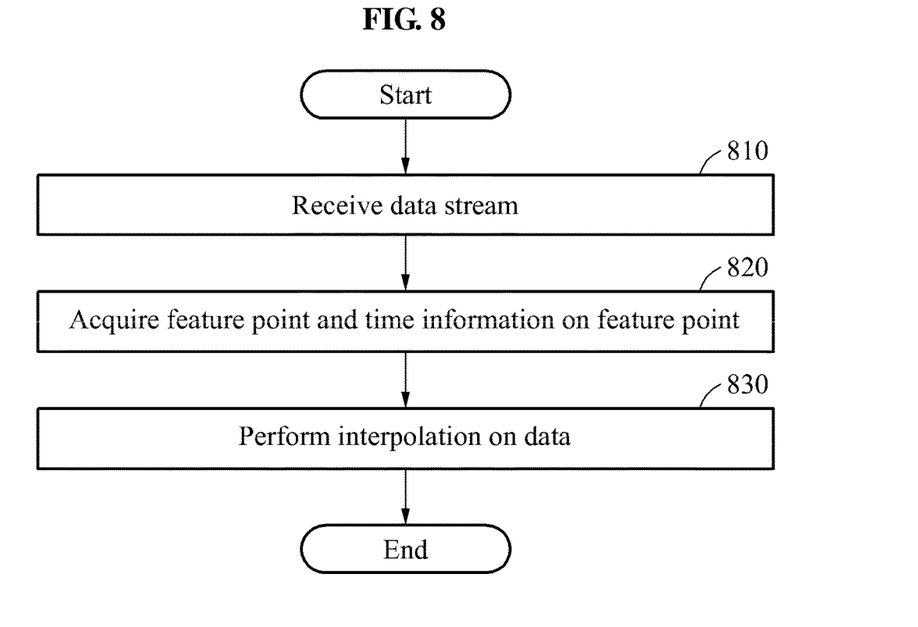
FIG. 8 illustrates a signal recovery method according to example embodiments.

FIG. 8 illustrates a signal recovery method according to example embodiments.

The signal recovery method may be performed by a signal recovery apparatus.

In operation 810, the signal recovery apparatus receives a data stream from an external apparatus.

In operation 820, the signal recovery apparatus acquires a feature point of a signal sensed by the external apparatus and time information on the feature point based on data acquired from the data stream.

In operation 830, the signal recovery apparatus determines an index of the feature point based on the time information, and performs an interpolation on the data based on a result of the determining.

Since the descriptions provided with reference to FIGS. 1 through 6 are also applicable here, repeated descriptions with respect to FIG. 8 will be omitted for increased clarity and conciseness.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like.

Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A signal processing apparatus comprising:
 a processor and a memory, the memory containing computer readable code that, when executed by the processor, configures the processor to,
  extract second samples from first samples based on a downsampling,
  identify a sample interval satisfying a reference using a change the second samples,
  acquire, a feature point based on a sample value of at least one sample included in the sample interval, the at least one sample being a member of the first samples,
  acquire time information corresponding to a time difference between a time associated with the feature point on the sample interval and a time associated with an adjacent one of the first samples adjacent to the feature point on the sample interval,
  add multiple of the feature point to the time information, and
  generate a data stream including the value of the feature point and the time information having added thereto the multiple of the feature point.

2. The signal processing apparatus of claim 1, wherein the processor is configured to transmit the data stream to a remote apparatus through a communication interface.

3. The signal processing apparatus of claim 1, wherein the at least one sample represents a motion of a user wearing a device including the signal processing apparatus.

4. The signal processing apparatus of claim 1, wherein the signal processing apparatus is embedded in a walking assistance device.

5. The signal processing apparatus of claim 1, wherein the feature point is an inflection point of the at least one sample.

6. A signal recovery apparatus comprising:
 a processor and a memory, the memory containing computer readable code that, when executed by the processor, configures the processor to,
  receive a data stream from an external apparatus,
  detect a feature point of a signal sensed by the external apparatus based on data acquired from the data stream,
  identify time information from data having a greatest value among the acquired data,
  determine an index of the feature point based on the time information, and
  interpolate the data based on a result of the processor determining the index to generate restored data, wherein
   the time information is a result of adding multiple of the feature point to time information corresponding to a time difference between a time associated with the feature point and a time associated with an adjacent one of first samples adjacent to the feature point.

7. The signal recovery apparatus of claim 6, wherein the processor is configured to upsample the acquired data.

8. The signal recovery apparatus of claim 6, wherein the external apparatus is a walking assistance device.

9. The signal recovery apparatus of claim 6, wherein the processor is configured to output the restored data.

10. The signal recovery apparatus of claim 6, wherein the processor is configured to analyze walking features of a user wearing the external apparatus based on the restored data.

11. A signal processing method comprising:
 extracting second samples from first samples based on a downsampling;
 identifying a sample interval satisfying a reference using a change in the second samples;
 acquiring, a feature point based on a sample value of at least one sample included in the sample interval, the at least one sample being a member of the first samples;
 acquiring time information corresponding to a time difference between a time associated with the feature point on the sample interval and a time associated with an adjacent one of the first samples adjacent to the feature point on the sample interval;
 adding multiple of the feature point to the time information; and
 generating a data stream including the value of the feature point and the time information having added thereto the multiple of the feature point.

12. The signal processing method of claim 11, wherein the acquiring comprises:
 acquiring a time difference between the feature point and an interval reference sample of a feature sample interval.

13. The signal processing method of claim 11, wherein the generating comprises:
 generating the data stream by applying the feature point and the time information as an interval reference sample of a feature sample interval.

14. The signal processing method of claim 11, further comprising:
 amplifying the time information.

15. The signal processing method of claim 11, further comprising:
 transmitting the data stream to a remote apparatus through a communication interface.

* * * * *